(12) United States Patent
Jackson

(10) Patent No.: US 6,730,089 B2
(45) Date of Patent: May 4, 2004

(54) NESTED CLOSURE PLUG AND SET SCREW WITH BREAK-OFF HEADS

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 101 days.

(21) Appl. No.: 10/227,754

(22) Filed: Aug. 26, 2002

(65) Prior Publication Data

US 2004/0039383 A1 Feb. 26, 2004

(51) Int. Cl.[7] .............................................. A61B 17/70
(52) U.S. Cl. ........................................ 606/61; 606/73
(58) Field of Search ............................. 606/60, 61, 72, 606/73; 411/2, 3, 5, 178, 393

(56) References Cited

U.S. PATENT DOCUMENTS

| | | |
|---|---|---|
| 2,243,717 A | 5/1941 | Moreira |
| 3,236,275 A | 2/1966 | Smith |
| 3,604,487 A | 9/1971 | Gilbert |
| 4,484,570 A | 11/1984 | Sutter et al. |
| 4,887,596 A | 12/1989 | Sherman |
| 5,005,562 A | 4/1991 | Cotrel |
| 5,067,955 A | 11/1991 | Cotrel |
| 5,129,388 A | 7/1992 | Vignaud et al. |
| 5,154,719 A | 10/1992 | Cotrel |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,346,493 A | 9/1994 | Stahurski et al. |
| 5,385,583 A | 1/1995 | Cotrel |
| 5,443,467 A | 8/1995 | Biedermann |
| 5,487,742 A | 1/1996 | Cotrel |
| 5,496,321 A | 3/1996 | Puno |
| 5,545,165 A | 8/1996 | Biedermann |
| 5,562,663 A | 10/1996 | Wisnewski et al. |
| 5,630,817 A | 5/1997 | Rokegem et al. |
| 5,643,260 A | 7/1997 | Doherty |
| 5,669,909 A | 9/1997 | Zdeblick et al. |
| 5,697,929 A | 12/1997 | Mellinger |
| 5,782,833 A | 7/1998 | Haider |
| 6,059,786 A | 5/2000 | Jackson |
| 6,063,090 A | 5/2000 | Schlapfer |
| 6,077,262 A | 6/2000 | Schlapfer et al. |
| 6,102,913 A | 8/2000 | Jackson |
| 6,224,598 B1 | 5/2001 | Jackson |

FOREIGN PATENT DOCUMENTS

WO  WO 94/10927  5/1994

OTHER PUBLICATIONS

*Spine,* Lipcott, Williams & Wilkins, Inc., vol. 24, No. 15, p.1495.

*Primary Examiner*—David O. Reip
(74) *Attorney, Agent, or Firm*—John C. McMahon

(57) ABSTRACT

A nested closure plug and set screw arrangement with break-off heads for securing a spinal fixation rod within to a bone screw includes a closure plug advanceable into an open channel of a bone screw and having a central threaded bore to receive a threaded set screw. The set screw is provided with a centrally positioned set point and a V-ring for cutting engagement with the surface of a clamped rod. The closure plug may be provided with a V-ring for the same purpose. The set screw V-ring is positioned and adapted to deform into engagement with the closure plug by engagement with the rod surface. By this means, the set screw and closure plug may be removed simultaneously. The closure plug and set screw have break-off installations which separate from their fasteners when pre-selected installation torques are exceeded.

32 Claims, 3 Drawing Sheets

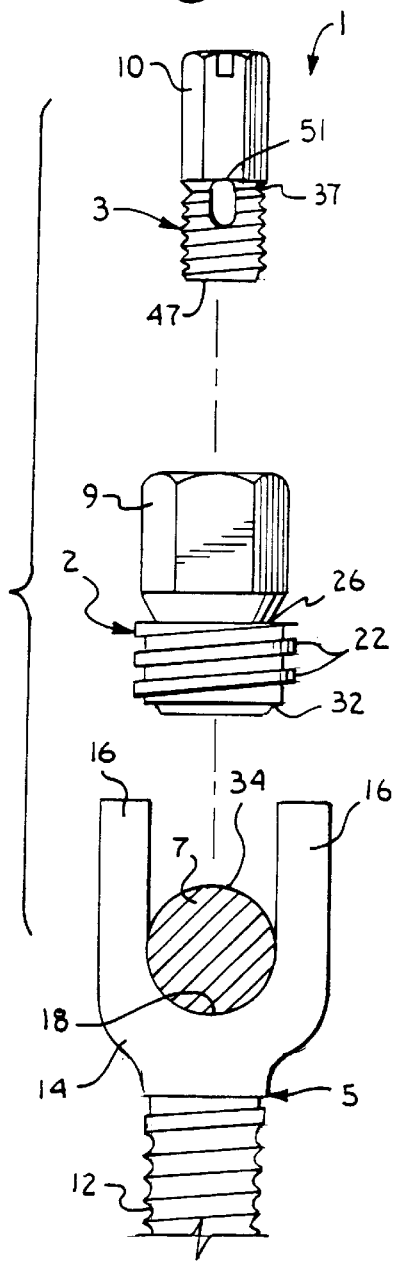
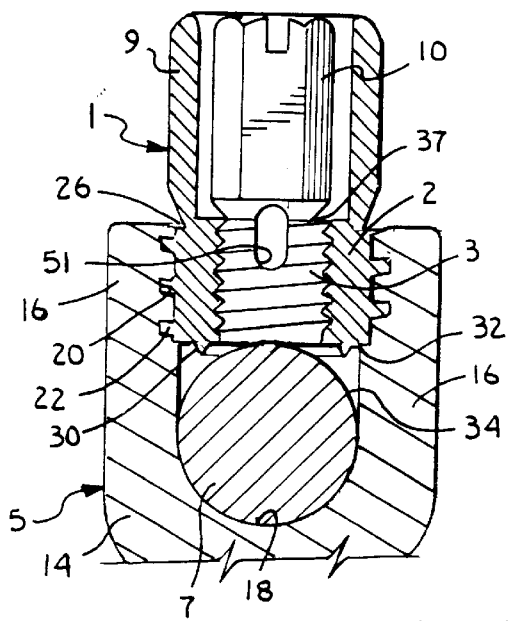
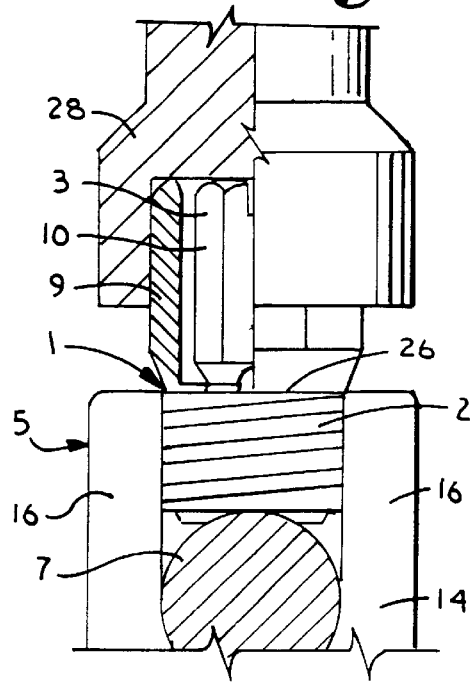

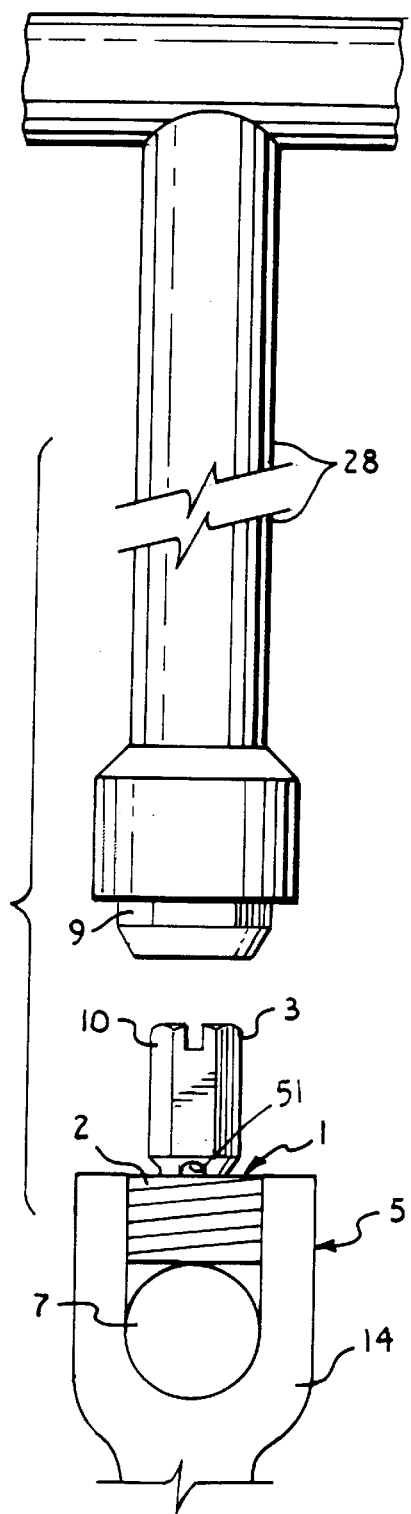
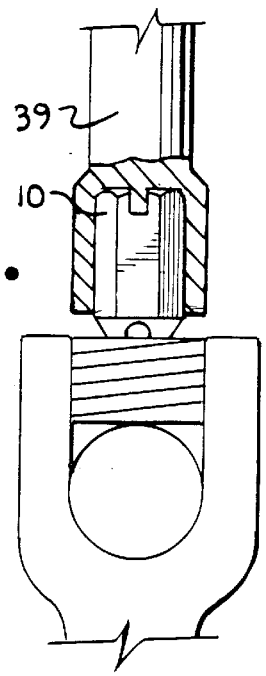
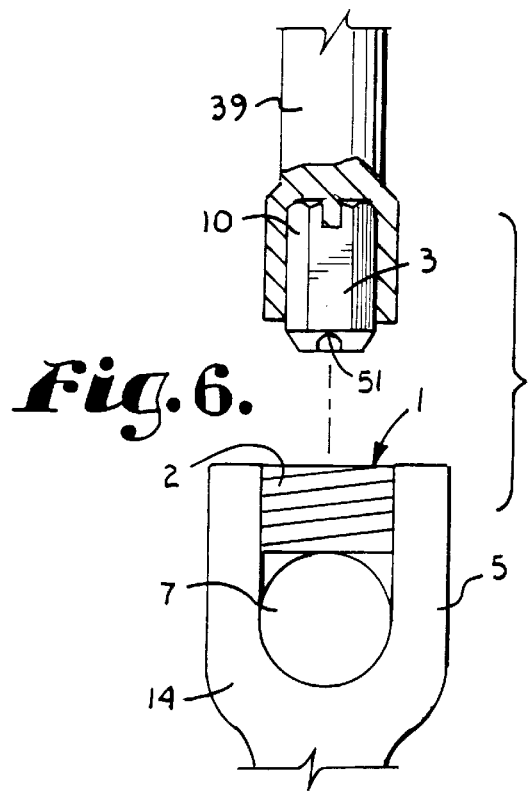

NESTED CLOSURE PLUG AND SET SCREW WITH BREAK-OFF HEADS

BACKGROUND OF THE INVENTION

The present invention is directed to a plug closure and set screw combination for medical implants and, more particularly, to a coaxially nested closure plug and set screw arrangement with individual break-off heads for the plug and screw.

Bone screws are utilized in many types of spinal surgery, such as for osteosynthesis, in order to secure various implants to vertebrae along the spinal column for the purpose of stabilizing and/or adjusting spinal alignment. Although both closed ended and open ended bone screws are known, open ended screws are particularly well suited for connections to rods and connector arms, because such rods or arms do not need to be passed through a closed bore, but rather can be laid or urged into an open receiver channel of such a head.

Typical open ended bone screws include a threaded shank with a pair of parallel projecting branches or arms which form a yoke with a U-shaped slot or channel to receive a rod. Hooks and other types of connectors, as are used in spinal fixation techniques, may also include open ends for receiving rods or projections from other structure. A rod is positioned in the U-shaped channel in generally perpendicular relation to the shank, and the open end of the yoke is closed off by a closure device. The closure device is tightened against the rod to clamp the rod in place against the bottom of the channel. The closure device must positively secure the rod in place to prevent rotational or translational movement of the rod relative to the bone screw and the bone in which it is anchored. Conventional types of closure devices include a threaded plug which is screwed into threads formed into the surfaces forming the U-shaped channel or an outer nut that goes around and is threaded on the arms.

Plug closures are often preferable to nuts because such take up less space. In order to perform the functions required of it, such a plug should be tightly torqued relative to the bone screw to effectively secure the bone screw to the rod and prevent relative rotation or translation. If the rod were straight, this could be more easily accomplished. However, in typical spinal fixation applications, the rod is almost always bent at the location of each bone screw to correctly position the rod for normal or desired curvature of the spinal column. Because the rod is bent, it does not flatly engage the bottom of the groove or U-shaped channel in the head of the bone screw, but tends to be raised from the bottom of the channel at one or both ends. Thus, when a conventional plug is installed, the outer periphery of the lower end of the plug most likely engages parts of the rod that are not set snugly against the floor of the channel opposite the plug. After installation, when the patient's back is bent during movement activities, the rod may flex slightly relative to the bone screw. Over time, such flexure may allow the rod to move, either translationally or rotationally, causing misalignment of the underlying vertebrae or cause the plug to work loose, because the conventional plug does not lock it securely in place.

What is needed is a plug which is particularly adapted to securely engage and lock in place relative to the bone screw a spinal rod which may be curved at the point of mutual contact.

SUMMARY OF THE INVENTION

The present invention provides an improved plug arrangement for securing a spinal fixation rod within an open-headed bone screw and including a cooperating set of a plug and a set screw with individual break-off heads. The bone screw has a threaded shank for screwing into a bone for anchorage to the bone and an open head with arms forming a U-shaped channel to receive a structural member such as a spinal fixation rod. A closure plug engages and is advanced into the open head using cooperating guide and advancement structure on the plug and channel arms, such as cooperating threads, to clamp the rod within the head channel.

Preferably, the guide and advancement structure is also of such a character as to resist splaying tendencies of the arms forming the channel. That is, the plug preferably resists the tendency of the arms to pull away from the plug when torque or force is applied to the plug and which would loosen the plug relative to the bone screw if splaying were allowed to occur. Guide and advancement structure that resists splaying includes, buttress threads, reverse angle threads and helical wound flange structure. The plug is bored and threaded to receive a set screw in a nested relationship within the plug to further secure the rod within the head. In particular, the set screw engages the rod intermediate the perimeter of the plug and where the rod is more likely to engage the bottom of the channel. This also produces multiple points of contact on the rod and cooperatively holds and locks the rod in a desired position relative to the bone screw.

The closure plug and the set screw have respective break-off installation heads to facilitate installation, produce a preferred installation torque and produce a low profile final assembly after the heads are broken off. The installation heads are connected respectively to the plug and set screw by weakened sections which are designed to fail at preselected levels of torque. Thus, the plug and set screw are both set with a preselected degree of tightness against the clamped rod by the level of torque at which the installation heads break off respectively from the plug and set screw.

The closure plug and set screw may include interference devices or formations such as a point, sharpened ring, knurling, at the bottom of each which cut into the rod and enhance the securing engagement of the plug and set screw with the clamped rod. In particular, a set screw may be provided with a centrally positioned set point and/or a "cup point" or annular V-shaped ring at the periphery of the rod engaging end of the set screw. The set point and V-ring operably cuts into the surface of the rod to positively engage the rod to thereby prevent translational and rotational movement of the rod relative to the bone screw. The plug may also be provided with a V-shaped ring to provide for more positive engagement of the plug with the rod. The point and V-rings may be used in combination to better secure the rod, especially when the rod is curved, since the interference devices engage the rod at multiple locations along the rod.

In the great majority of cases, spinal fixation systems are permanently implanted. However, there are situations in which it is necessary to remove, replace, or repair components of an implanted fixation system. For example, such an adjustment might be necessary during implant surgery to adjust the position or alignment of a rod. An adjustment might be necessary after surgery to relieve an undesired pressure or tension which was not detected during surgery. Adjustments might also be required to treat an injury which occurs after the fixation system has been implanted. For these reasons, provisions are made for removal of the plug and set screws of the present invention from the bone screw heads. The set screw of the present invention is provided with structure to enable positive, non-slip engagement of the set screw by a removal tool, such as a pair of diametrically slots which are located at the top face of the set screw and extend partly inward from the periphery, but do not intersect. The closure plug may or may not need separate removal structure. Preferably, the lower part of the set screw deforms on installation so as to interferingly engage the plug, so that the set screw becomes secured to the closure plug in such a manner that rotation of a removal tool engaged with the set screw causes both the set screw and closure plug to be removed substantially as a unit from the head of the bone screw.

OBJECTS AND ADVANTAGES OF THE INVENTION

Therefore, the objects of the present invention include: providing an improved bone screw arrangement for implantation into a vertebra of a patient; providing such a bone screw arrangement including a threaded bone screw for implanting into a bone such as a vertebra and having an open head formed by a pair of spaced apart arms defining a U-shaped channel to receive a structural member such as a spinal fixation rod; providing such an arrangement including a closure plug which is secured within the channel by a guide and advancement structure such as cooperating threads on the closure plug and inner surfaces forming the channel, to thereby clamp the rod to the bone screw; providing such an arrangement in which the closure plug is bored and tapped to receive a set screw nested therein to further secure the spinal fixation rod within the bone screw head; providing such an arrangement in which both the closure plug and set screw have torque limiting break-off heads so the arrangement has a low profile after final installation and to control the level of torque at which the closure plug and set screw are installed is controlled at a preselected level; providing such an arrangement in which the set screw and also the closure plug have rod surface interference formations thereon for securely engaging the clamped rod against translational and/or rotational movement relative to the bone screw by cutting into the surface of the rod; providing such an arrangement which is particularly effective in securing rods which are curved in the vicinity of the bone screw by engaging the rod at multiple locations; providing such an arrangement in which the set screw has a centrally located set point and a peripherally located V-shaped ring for cutting into the surface of the clamped rod when the set screw is torqued tightly; providing such an arrangement wherein the closure plug has a V-shaped ring formed thereon to cut into the surface of the clamped rod to more securely engage the rod; providing such an arrangement in which the set screw is provided with formations to enable non-slip engagement by a removal tool; providing such an arrangement in which the set screw has a diametrically opposed side slots extending from the periphery partially inward across an outer face for engagement by a removal tool with the side slots being accessible when the head of the set screw breaks away; providing such an arrangement including provisions for removal of the closure plug; providing such an arrangement in which the V-ring of the set screw is formed and positioned in such a manner that the V-ring is deformed into securing engagement with the closure plug by engagement of the V-ring with the surface of the rod; and providing such a nested closure plug and set screw arrangement with break-off heads for clamping a rod to a bone screw which is economical to manufacture, which is compact and secure in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded elevational view illustrating components of a nested closure plug and set screw arrangement with break-off heads which embodies the present invention.

FIG. 2 is an enlarged fragmentary cross sectional view showing the nested closure plug and set screw positioned within a channel of a bone screw prior to final setting of the plug and set screw.

FIG. 3 is a side view of the arrangement illustrating a closure plug installation tool engaging the closure plug to torque it into clamping or set engagement with a rod and to eventually separate a plug installation head from the plug at a preselected torque with portions broken away to illustrate detail thereof.

FIG. 4 is a side elevational view of the nested plug and set screw arrangement at a reduced scale and illustrates the plug installation tool separating the plug installation head from the closure plug.

FIG. 5 is a side elevational view similar to FIG. 4 and illustrates engagement of a set screw installation tool with the breakoff installation head of the set screw to allow the installer to torque the set screw into a set or clamping engagement with the rod with portions broken away to illustrate detail.

FIG. 6 is a view similar to FIG. 5 and illustrates the set screw installation tool separating the installation head from the set screw with portions broken away to illustrate detail.

DETAILED DESCRIPTION OF THE INVENTION

Figure 7:
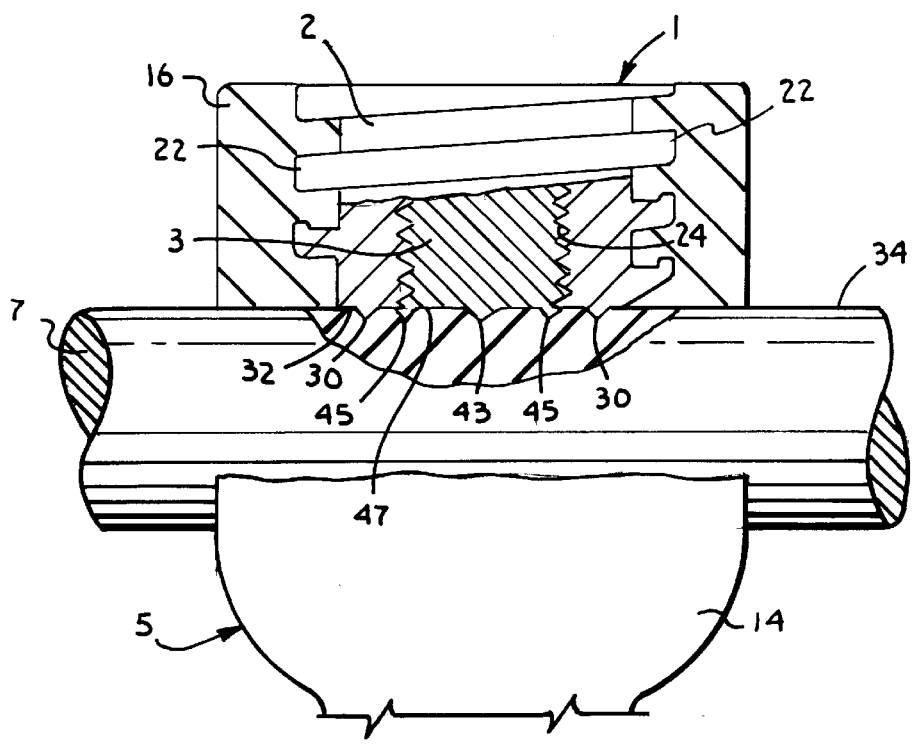
FIG. 7 is a greatly enlarged fragmentary front elevational view, with portions broken away so as to be partially in cross section, and illustrates multiple locations of engagement of the plug and set screw with the rod.
Figure 8:
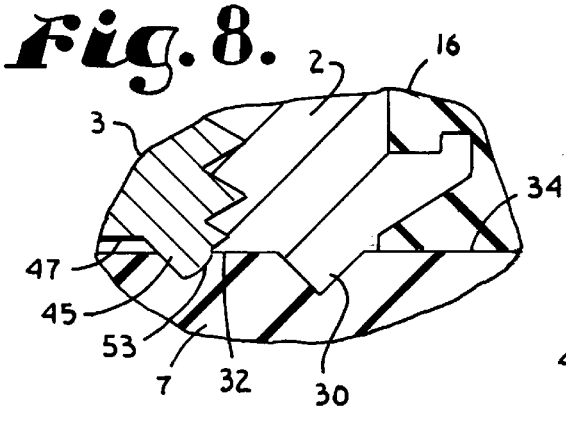
FIG. 8 is a further enlarged fragmentary cross sectional view showing deformation of a V-shaped ring of the set screw upon interfering engagement with the surface of the rod.
Figure 9:
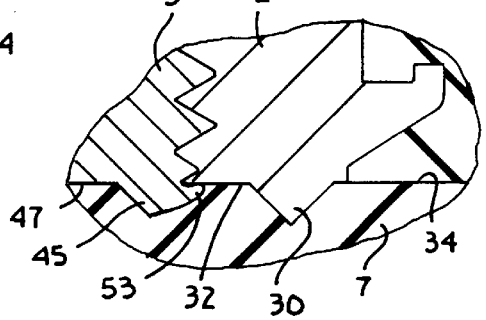
FIG. 9 is a view similar to FIG. 8 and shows deformation of the set screw V-ring into securing engagement with the closure plug to enable removal of the plug with the set screw.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a nested closure plug and set screw arrangement with break-off heads which embodies the present invention. The arrangement 1 generally includes a closure plug 2 and a set screw 3 which cooperate with a bone screw 5 to close an open head thereof and to clamp a spinal fixation rod 7 within the bone screw 5. The closure plug 2 and set screw 3 have respective break-off installation heads 9 and 10 which separate from their respective fastener 2 or 3 when installation torque exceeds selected levels.

The bone screw 5 includes a threaded shank 12 for threaded implanting or anchoring in a bone (not shown) such as a vertebra. The bone screw 5 includes an open head 14 formed by spaced apart arms 16 which define a U-shaped channel 18 to receive a spinal fixation structure member such as the rod 7. The rod receiving channel 18 is sized so that the rod 7 fits snugly therein to maximize clamping or frictional engagement of the rod 7 with surfaces forming the channel 18. Inner surfaces of the arms 16 are provided with guide and advancement formations, such as internal threads 20, a helically wound flange, or the like, to interferingly receive and advance the plug 2 into clamping engagement with the rod 7 when the plug 2 is rotated.

The closure plug 2 is generally cylindrical and has a mating external guide and advancement formation on an external surface, such as a helical thread 22 which is complementary to and compatible with the threads 20 of the bone screw head 14. The threads 20 and 22 are preferably of a type that do not exert radially outward forces on the arms 16 and thereby avoid tendencies toward splaying of the arms 16 of the bone screw head 14, when the closure plug 2 is tightly torqued into the head 14. The closure plug 2 has an internally threaded bore 24 which is centrally located to receive the threaded set screw 3 therein.

The closure plug 2 is provided with the break-off head 9 which is connected to the plug 2 by a weakened region 26. The weakened region 26 is dimensioned in thickness to control the torque at which the break-off head 9 separates from the plug 2. The preselected separation torque of the weakened region 26 is designed to provide secure clamping of the rod 7 by the plug 2 before the head 9 separates, for example 100 inch pounds of force may in some instances be the selected break off torque. The illustrated break-off head 9 has an external hexagonal shape to enable positive, non-slip engagement of the head 9 by a plug installation tool 28 (FIGS. 3 and 4). Separation of the installation head 9 leaves only the more compact of the closure plug 2, so that the installed plug 2 has a low profile which is important in a device implanted in a living body.

The closure plug 2 may include provisions to enhance the clamping engagement of it with the rod 7. The illustrated plug 2 has a so-called "cup point" or V-shaped ridge or ring 30 on an inner end 32 of the plug 2. The V-ring 30 operably cuts into a surface 34 of the rod 7 during assembly, when the plug 2 is threaded into the screw head 14, so that the plug more positively secures the rod against rotational and translational movement of the rod relative to the head 15 of the bone screw 5. Alternatively, it is foreseen that other clamp enhancing structure, such as knurling may be employed. And in some arrangements, no such clamp enhancing structure may be necessary or desirable.

The set screw 3 is generally cylindrical in shape and is sized and threaded for placement in the threaded bore 24 of the closure plug 2 in a nested relationship therewith. The set screw 3 includes the break-off head 10 which is connected thereto by a weakening groove or ring 37 which is dimensioned in thickness and/or cross section in such a manner as to fail when torque between the head 10 and the screw 3 exceeds a pre-selected separation torque, causing the head 10 to separate from the remainder of the screw 3. The illustrated break-off head 10 is hexagonal in shape for positive, non-slip engagement by a set screw installation tool 39 (FIGS. 5 and 6).

The set screw 3 preferably includes structure for enhancing clamping or setting engagement with the surface 34 of the rod 7. The illustrated set screw 3 has a centrally located set point 43 and a peripherally located cup point or V-shaped set ring 45 on an inner end 47 of the screw 3. The set point 43 and set ring 45 cut into the surface 34 of the rod 7 when the set screw 3 is tightly torqued into the closure plug 2. It is foreseen that other structures for enhancing clamping, such as knurling or the like may be used in some situations or none in others.

There are circumstances under which it is desirable or necessary to release the rod 7 from the bone screw 5. For example, it might be necessary for a surgeon to readjust components of a spinal fixation system, including the rod 7, during an implant procedure, following an injury to a person with such a system implanted, or the like. The set screw 3 is provided with side slots 51 for positive, non-slip engagement by a set screw removal tool (not shown). It is foreseen that other removal structures such as a tool receiving aperture that becomes accessible after the head 10 breaks from the remainder of the screw 3 may be used to remove the body of the screw 3 after the body is set.

Similarly, it may be necessary to remove the closure plug 2 from the head 14 of the bone screw 5 to complete the release of the rod 7. The closure plug 2 could be provided with removal structure that becomes accessible when the head 9 breaks from the plug 2 through engagement by an appropriate closure plug removal tool (not shown). However, in the illustrated arrangement 1, the V-ring 45 of the set screw 3 is positioned at such a diameter and is formed in such a manner that an edge portion 53 of the V-ring 45 is preferably deformed into snug engagement with the inner end 32 of the closure plug 2. Thus, engagement of the V-ring 45 with the surface 34 of the rod 7 deforms the V-ring 45, as it cuts into the surface 34, thereby producing the deformed edge 53 which is, further, crushed into frictional engagement with the end surface 32 of the closure plug 2, adjacent an inner end of the threaded bore 24. Thus, after installation is complete, the set screw 3 is effectively joined with the closure plug 2, whereby engagement of the set screw 3 by a removal tool and rotation of the set screw 3 also backs the closure plug 2 out of the threads 20 in the arms 16 of the bone screw 14, thereby releasing the rod 7 for removal from the bone screw 5 or repositioning of the rod 7.

In typical use, the set screw 3 is pre-assembled within the closure plug 2 for the surgeon's convenience. Each of a number of bone screws 5 is threaded into selected bones, such as a vertebrae, and a rod, such as the rod 7, is placed in the channel 18 of the head 14 of each bone screw 5. Thereafter, a closure plug 2, with set screw 3 threaded into the bore 24 thereof, is threaded into each bone screw head 14. The closure plugs 2 are then tightened in a selected order with or without bending of the rod to achieve and maintain the desired alignment of the spine. As each closure plug 2 is tightened, the installation head 9 breaks off at a pre-selected plug separation torque. Finally, the set screws 3 are tightened in a selected order, resulting in separation of the set screw installation heads 10 at their pre-selected set screw separation torque. As each set screw 3 is torqued tightly, it is joined with its closure plug 2 by deformation of its V-ring 45. If the closure plug 2 is provided with a V-ring 30, the combination of the closure plug 2 and set screw 3 preferentially provides five points of positive engagement of the fastener combination along a rod 7, including the V-ring 30 at two locations, the V-ring 45 at two locations, and the set point 43 at a single location. The availability of multiple locations of engagement of the plug 2 and set screw 3 with the rod 7 increases the probability that the rod 7 will be engaged securely by the nested closure plug 2 and set screw 3.

If it should be necessary to release the rod 7 at a particular location, a removal tool is engaged with the side slots 51 of the set screw 3 to remove the set screw 3 and the closure plug 2 which is frictionally joined thereto from the particular bone screw 5.

It is noted that when the set screw 3 and plug 2 are used the set screw 3 is coaxially nested in the plug 2 prior to break off of the heads 9 and 10. The plug 2 normally first advanced and torqued until a first preselected torque is achieved at which time the head 9 breaks from the remainder of the plug 2 and leaves the remainder of the plug 2 in an installed configuration in which it normally engages and clamps the rod 7. However, the plug 2 may only seat at the bottom of the opening or channel 18 so as to close the channel 18 and capture the rod 7 therein. The set screw is then normally torqued to a second preselected torque to engage, abut and secure the rod 7. In some instances the first and second preselected torques will be the same (for example, 100 inch pounds) and in other situations it may be desirable to have different torques.

It is to be understood that while certain forms of the present invention have been illustrated and described herein, it is not to be limited to the specific forms or arrangement of parts described and shown.

What is claimed and desired to be secured by Letters Patent is:

1. A nested closure plug and set screw combination for securing a structural element within a receiver of a medical implant having a plug receiving opening, said combination comprising:
    (a) a closure plug adapted to be interferingly positioned within the plug receiving opening of the structural element receiver so as to close the opening when in an installed configuration, said plug having a threaded bore formed therein;
    (b) a threaded set screw operably threadably received in said bore of said plug and having a setting configuration wherein said set screw is in engagement with the structural element;
    (c) said plug having a break-off plug head which operably breaks from said plug at a first preselected torque; and
    (d) said set screw having a break-off screw head that breaks from said set screw at a second preselected torque when in said setting configuration.
2. The combination as set forth in claim 1 wherein:
    (a) said closure plug includes an external guide and advancement structure which operably cooperates with complementary structure within a structural element receiver to interferingly position said plug within the plug receiving opening within the receiver, said guide and advancement structure enabling advancement of said plug into said engagement in response to rotation of said plug.
3. The combination as set forth in claim 1 wherein:
    (a) said closure plug includes an external plug thread which operably cooperates with a complementary internal plug thread within a structural element receiver to interferingly position said plug within the plug receiving opening within the receiver, said external plug thread and internal plug thread enabling advancement of said plug into said engagement in response to rotation of said plug.
4. The combination as set forth in claim 1 wherein:
    (a) said closure plug has a plug end interference feature which is shaped and positioned to operably cut into a surface of the structural element in said installed configuration.
5. The combination as set forth in claim 1 wherein:
    (a) said closure plug has a plug end set ring which is shaped and positioned to operably cut into a surface of the structural element in said installed configuration.
6. The combination as set forth in claim 1 wherein:
    (a) said set screw has a screw end interference feature which is shaped and positioned to operably cut into a surface of the structural element in said setting configuration.
7. The combination as set forth in claim 1 wherein:
    (a) said set screw has a screw end set ring which is shaped and positioned to operably cut into a surface of the structural element in said setting configuration.
8. The combination as set forth in claim 1 wherein:
    (a) said set screw has a screw end set point which is shaped and positioned to operably cut into a surface of the structural element in said setting configuration.
9. The combination as set forth in claim 1 wherein:
    (a) said set screw has a screw tool engagement feature to enable non-slip engagement of said set screw by a set screw removal tool.
10. The combination as set forth in claim 1 wherein:
    (a) at least one said set screw or said plug has a joining feature which forms a non-slip joining of said plug and said set screw when said set screw is threaded into said setting configuration to provide for simultaneous removal of said plug when said set screw is removed from said setting configuration.
11. The combination as set forth in claim 1 wherein:
    (a) said set screw has a screw end set ring which is shaped and positioned to operably cut into a surface of the structural element in said setting configuration; and
    (b) said set ring is positioned, shaped, and formed in such a manner as to promote deformation of said set ring into frictional engagement and joining relationship with said plug whereby said plug is removed from the installation configuration thereof when said set screw is removed from said setting configuration.
12. The combination as set forth in claim 1 wherein:
    (a) said break-off plug head surrounds said set screw head prior to said plug head breaking from said plug.
13. The combination as set forth in claim 12 wherein:
    (a) said set screw and said plug are coaxial during use and said break-off screw head is connected to said set screw in such a manner that torque between said screw head and said set screw exceeding said second preselected torque causes said screw head to separate from a remainder of said set screw subsequent to said plug head separating from a remainder of said plug.
14. A nested closure plug and set screw arrangement for operably securing a structural element of a medical implant within a receiver having a plug receiving opening, said arrangement comprising:
    (a) a closure plug adapted to be interferingly positioned within the plug receiving opening of the structural element receiver when in an installed configuration, said plug having a threaded coaxial bore formed therein;
    (b) a threaded set screw threaded into said bore of said plug and into engagement with the structural element when in a setting configuration;
    (c) said plug having a break-off plug head;
    (d) said set screw having a break-off screw head;
    (e) said closure plug including an external guide and advancement structure which is adapted to cooperate with complementary structure within the structural element receiver to operably interferingly position said plug within the plug receiving opening within the receiver, said guide and advancement structure enabling advancement of said plug into said installed configuration in response to rotation of said plug;

(f) said closure plug including a plug end interference feature which is shaped and positioned to operably cut into a surface of the structural element when in the installed configuration;

(g) said set screw including a screw end interference feature which is shaped and positioned to operably cut into a surface of the structural element in said setting configuration; and (h) at least one said set screw or said plug has a joining feature which forms a non-slip juncture of said plug and said set screw when said set screw is threaded into said setting configuration with the structural member to provide for simultaneous removal of said plug when said set screw is removed from said setting configuration.

15. The arrangement as set forth in claim 14 wherein:
(a) said closure plug includes an external plug thread which is adapted to operably cooperate with a complementary internal thread within the structural element receiver to interferingly position said plug within a plug receiving opening within such a receiver, engagement of said external plug thread and the internal thread during installation enabling advancement of said plug into said installed configuration in response to rotation of said plug.

16. The arrangement as set forth in claim 14 wherein said plug end interference feature includes:
(a) a plug end set ring which is shaped and positioned to be adapted to operably cut into a surface of a structural element in said installed configuration.

17. The arrangement as set forth in claim 14 wherein said screw end interference feature includes:
(a) a screw end set ring which is shaped and positioned to be adapted to operably cut into a surface of the structural element in said setting configuration; and
(b) a screw end set point which is shaped and positioned to be adapted to operably cut into said surface of the structural element in said setting configuration.

18. The arrangement as set forth in claim 14 wherein:
(a) said set screw has a screw tool engagement feature to enable non-slip engagement of said set screw by a set screw removal tool.

19. The arrangement as set forth in claim 14 wherein said joining feature includes:
(a) said set screw having a screw end set ring which is shaped and positioned to operably cut into a surface of the structural element in said setting configuration; and
(b) said set ring being positioned, shaped, and formed in such a manner as to promote deformation of said set ring into joining relationship to said plug when torqued to said setting configuration, whereby said plug is secured to and removed from said set screw when said set screw is removed from said setting configuration.

20. The arrangement as set forth in claim 14 wherein:
(a) said break-off plug head is connected to said closure plug in such a manner that torque between said plug head and said plug that exceeds a preselected plug head torque causes said plug head to separate from said closure plug.

21. The arrangement as set forth in claim 14 wherein:
(a) said break-off screw head is connected to said set screw in such a manner that torque between said screw head and said set screw that exceeds a preselected screw head torque causes said screw head to separate from said set screw.

22. The arrangement as set forth in claim 14 including:
(a) the structural element and the receiver; and
wherein
(b) said structural element is a rod and said receiver is a bone screw having a pair of spaced arms forming said opening there between.

23. In a nested closure plug and set screw arrangement adapted to secure a structural element within a receiver having a plug receiving opening and including a closure plug adapted to be operably interferingly positioned within the plug receiving opening and in an installed configuration with the structural element positioned within the receiver and said plug having a threaded bore formed therein and further a set screw threadably received in said bore of said plug; the improvement comprising:
(a) said closure plug having a break-off plug head; and
(b) said set screw having a break-off screw head nested prior to break off of said closure plug head within said closure plug head.

24. The arrangement as set forth in claim 23 wherein:
(a) said closure plug includes an external guide and advancement structure which is adapted to cooperate with complementary structure within a structural element receiver to interferingly position said plug within a plug receiving opening within the receiver, said guide and advancement structure enabling advancement of said plug into said installed configuration in response to rotation of said plug.

25. The arrangement as set forth in claim 23 wherein:
(a) said closure plug has a plug end interference feature which is shaped and positioned so as to be adapted to operably cut into a surface of the structural element in said installed configuration.

26. The arrangement as set forth in claim 23 wherein:
(a) said set screw has a screw end interference feature which is shaped and positioned so as to be adapted to operably cut into a surface of the structural element in said setting configuration.

27. The arrangement as set forth in claim 23 wherein:
(a) said set screw has a screw tool engagement feature to enable non-slip engagement of said set screw by a set screw removal tool.

28. The arrangement as set forth in claim 23 wherein:
(a) at least one of said set screw or said plug has a joining feature which forms a non-slip juncture of said plug and said set screw when said set screw is threaded into said setting configuration to provide for simultaneous removal of said plug from said receiver, when said set screw is removed from said setting configuration.

29. The arrangement as set forth in claim 23 wherein:
(a) said break-off plug head is connected to said closure plug in such a manner that torque between said plug head and said plug that exceeds a preselected plug head torque causes said plug head to separate from said closure plug.

30. The arrangement as set forth in claim 23 wherein:
(a) said break-off screw head is connected to said set screw in such a manner that torque between said screw head and said set screw that exceeds a preselected screw head torque causes said screw head to separate from said set screw.

31. The arrangement as set forth in claim 23 including:
(a) the receiver and the structural element; and
wherein
(b) said receiver is a bone screw and said structural element is a spinal rod.

32. In a closure plug and set screw combination wherein the closure plug is adapted to close an opening in a medical implant and capture a structural member therein and wherein said plug includes a central bore with a set screw received in said bore; the improvement comprising:
(a) a joining structure at a lower end of at least one of said plug and set screw that operably engages and forms a juncture with the opposite of said plug and set screw upon torquing of said set screw so that said plug joins with said set screw for removal.

* * * * *